US009320514B2

(12) United States Patent
Rohlinger et al.

(10) Patent No.: US 9,320,514 B2
(45) Date of Patent: *Apr. 26, 2016

(54) SUTURE ANCHOR

(71) Applicant: REDYNS MEDICAL LLC, Los Angeles, CA (US)

(72) Inventors: George J. Rohlinger, Coeur d'Alene, ID (US); Nathan B. Snyder, Los Angeles, CA (US)

(73) Assignee: Redyns Medical LLC, Los Angeles, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/717,066

(22) Filed: May 20, 2015

(65) Prior Publication Data

US 2015/0250473 A1 Sep. 10, 2015

Related U.S. Application Data

(62) Division of application No. 13/430,201, filed on Mar. 26, 2012, now Pat. No. 9,039,739.

(60) Provisional application No. 61/467,635, filed on Mar. 25, 2011.

(51) Int. Cl.
*A61B 17/04* (2006.01)
*A61B 17/00* (2006.01)
*A61B 17/122* (2006.01)

(52) U.S. Cl.
CPC ......... *A61B 17/0401* (2013.01); *A61B 17/1227* (2013.01); *A61B 2017/00526* (2013.01);
(Continued)

(58) Field of Classification Search
CPC ........... A61B 17/0401; A61B 17/1227; A61B 2017/00526; A61B 2017/0403; A61B 2017/0446; A61B 2017/0412; A61B 2017/0414; A61B 2017/0437; A61B 2017/0445; A61B 2017/0464
USPC ................. 606/232, 148, 151, 228, 213, 233; 623/1.15
See application file for complete search history.

(56) References Cited

U.S. PATENT DOCUMENTS 5,209,756 A  5/1993  Seedhom et al.
5,222,961 A  6/1993  Nakao et al.
(Continued)

FOREIGN PATENT DOCUMENTS

EP  0 594 002  4/1994
WO  94/15535  7/1994
(Continued)

OTHER PUBLICATIONS

International Search Report and Written Opinion (PCT/US2012/030608); Sep. 25, 2012.
(Continued)

*Primary Examiner* — Julie A Szpira
(74) *Attorney, Agent, or Firm* — Dunlap Codding, P.C.

(57) ABSTRACT

A method of forming a suture anchor comprising a one piece blank folded to form a body. The body has a floor, a first sidewall extending from one end of the floor and a second sidewall extending from an opposite end of the floor. A recess is defined by the floor, first sidewall and second sidewall. A crossbar extends inwardly from the second sidewall across the recess such that a free end of the crossbar is normally disposed distally of a transverse edge of the body. The crossbar is flexible such that when a distally directed force is applied, the free end of the crossbar is positionable in the recess. The free end of the crossbar is engageable with the transverse edge to limit the proximal motion of the crossbar from a proximally directed force.

8 Claims, 8 Drawing Sheets

(52) U.S. Cl.
CPC . *A61B2017/0403* (2013.01); *A61B 2017/0412* (2013.01); *A61B 2017/0414* (2013.01); *A61B 2017/0437* (2013.01); *A61B 2017/0445* (2013.01); *A61B 2017/0446* (2013.01); *A61B 2017/0464* (2013.01)

(56) References Cited

U.S. PATENT DOCUMENTS

| | | | |
|---|---|---|---|
| 5,980,558 | A | 11/1999 | Wiley |
| 6,024,758 | A | 2/2000 | Thal |
| 6,336,928 | B1 | 1/2002 | Guerin et al. |
| 6,773,437 | B2 | 8/2004 | Ogilvie et al. |
| 7,914,574 | B2 | 3/2011 | Schmid et al. |
| 8,088,163 | B1 | 1/2012 | Kleiner |
| 2004/0098050 | A1 | 5/2004 | Foerster et al. |
| 2004/0153153 | A1 | 8/2004 | Elson et al. |
| 2009/0088798 | A1 | 4/2009 | Snyder et al. |
| 2009/0292313 | A1 | 11/2009 | Anspach, III et al. |
| 2010/0121355 | A1 | 5/2010 | Gittings et al. |
| 2011/0152928 | A1 | 6/2011 | Colleran et al. |
| 2011/0313453 | A1 | 12/2011 | Krumme et al. |
| 2012/0053622 | A1 | 3/2012 | Schulman |

FOREIGN PATENT DOCUMENTS

| | | |
|---|---|---|
| WO | 2010/121234 | 10/2010 |
| WO | 2012/135141 | 10/2012 |

OTHER PUBLICATIONS

Supplementary European Search Report (EP 12763219.8); Feb. 27, 2015.

SUTURE ANCHOR

CROSS REFERENCE TO RELATED APPLICATIONS

This application is a divisional of U.S. Ser. No. 13/430,201, filed Mar. 26, 2012, which claims priority to U.S. Provisional Application Ser. No. 61/467,635, filed Mar. 25, 2011, each of which is hereby incorporated herein in their entirety.

BACKGROUND

In many situations soft tissue may need to be attached (or re-attached) to bone. As an example, a ligament or tendon may have been detached from bone as the result of injury, and appropriate repair may require re-attaching the ligament or tendon to its host bone. The use of sutures together with one or suture anchors is one way of attaching soft tissue to bone. Suture anchors generally include a body that is deployed in bone with one or more sutures extending from the body. The sutures may then be used to secure the soft tissue to the bone, e.g., by passing the sutures through the tissue and then knotting the suture so as to hold the tissue in position relative to the bone.

Many suture anchors are configured such that the sutures need to be attached to the suture anchor either at the time of manufacture or in the operating room prior to use. In either case, the sutures are attached to the body of the suture anchor prior to deployment of the suture anchor in the body. As a result, a surgeon may be constrained by the configuration of the suture anchor once it has been deployed in the body. In other words, with many suture anchor constructions, the number and types of sutures selected by the surgeon prior to deployment in the bone significantly constrains the choices available to the surgeon after the suture anchor has been deployed in the bone. This can be a significant limitation, since in many circumstances the surgeon may wish to adjust a procedure in response to tissue conditions which may only become apparent after the procedure has commenced.

A suture anchor has been suggested that permits sutures to be loaded into the suture anchor after the suture anchor has been deployed in the bone. Such a suture anchor is disclosed in U.S. Publication No. 2009/0088798 by Snyder et al. The suture anchor disclosed in the '798 application includes a body having a proximal end, a distal end, an outer surface, and an axial recess extending from the proximal end toward the distal end. A flexible finger or crossbar extends from the body and across the axial recess such that when a distally directed force is applied to the crossbar, a suture may be passed by the crossbar and when a proximally directed force is applied to the suture, the crossbar is captured to limit proximal motion of the crossbar and thereby capture the suture.

The inventive concepts disclosed herein are directed to a suture anchor similar in construction and function, but which is formed from a blank.

DETAILED DESCRIPTION OF EXEMPLARY EMBODIMENTS

Before explaining at least one embodiment of the presently disclosed and claimed inventive concepts in detail, it is to be understood that the presently disclosed and claimed inventive concepts are not limited in their application to the details of construction, experiments, exemplary data, and/or the arrangement of the components set forth in the following description or illustrated in the drawings. The presently disclosed and claimed inventive concepts are capable of other embodiments or of being practiced or carried out in various ways. Also, it is to be understood that the phraseology and terminology employed herein is for purpose of description and should not be regarded as limiting.

Figure 1:
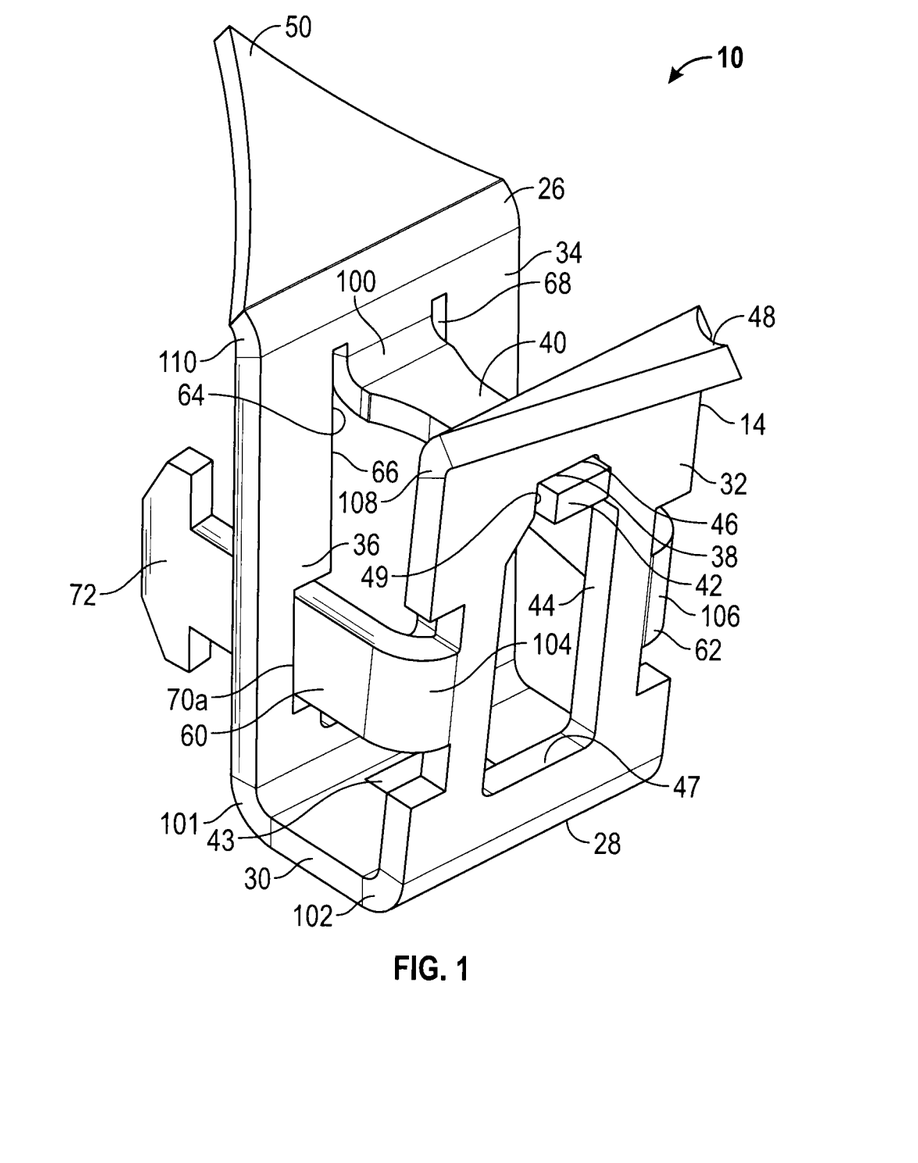
FIG. 1 is a perspective view of a suture anchor constructed in accordance with the inventive concepts disclosed herein.
Figure 2:
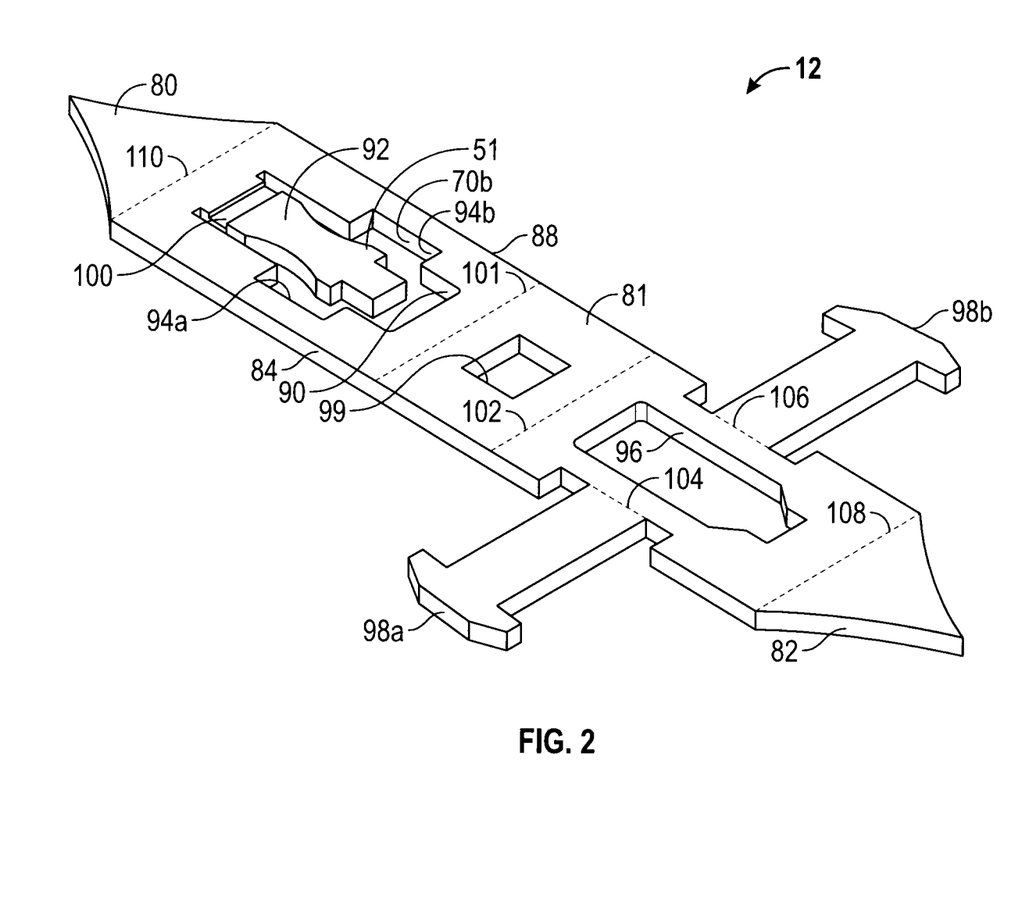
FIG. 2 is a perspective view of a blank for forming the suture anchor of FIG. 1.

Referring to the drawings, and more particularly to FIGS. 1 and 2, a suture anchor 10 constructed in accordance with the inventive concepts disclosed herein is illustrated. The suture anchor 10 is formed from a one piece blank 12 (FIG. 2) folded to form a body 14. The body 14 has a proximal end 26, a distal end 28, a floor 30, a first sidewall 32 extending from one end of the floor 30 toward the proximal end 26, and a second sidewall 34 extending from an opposite end of the floor 30 toward the proximal end 26. The floor 30, the first sidewall 32, and the second side wall 34 cooperate to define a recess 36. The first sidewall 32 is provided with a transverse edge 38, and the second sidewall 34 has a crossbar 40 extending inwardly therefrom across the recess 36 such that a free end 42 of the crossbar 40 is normally disposed distally of the transverse edge 38. The floor 30 may be provided with a central opening 43 configured to receive a portion of an anchor insertion tool for deploying the suture anchor 10 in bone.

The crossbar 40 is flexible such that when a distally directed force is applied to the crossbar 40, the free end 42 of the crossbar 40 is positioned in the recess 36 and when a proximally directed force is applied to the crossbar 40 such as by a suture which is looped over the crossbar 40, the free end 42 of the crossbar 40 engages with the transverse edge 38 to limit proximal motion of the crossbar 40.

In one embodiment, the first sidewall 32 is provided with a crossbar window 44 which is in communication with the recess 36. The crossbar window 44 has a proximal side 46 and a distal side 47 where the proximal side 46 of the crossbar window 44 defines the transverse edge 38. The crossbar 40 extends across the recess 36 such that the free end 42 of the crossbar 40 is normally disposed in the crossbar window 44. The crossbar window 44 may be formed to have a crossbar receiving slot 49 having a width that is less than the remaining portion of the crossbar window 44. The crossbar receiving slot 49 is formed by tapering the crossbar window 44 to a width that is substantially equal to the width of the free end 42 of the crossbar 40 so that the crossbar 40 is guided into the crossbar receiving slot 49 of the crossbar window 44. The crossbar receiving slot 49 is shown to be positioned along a center line of the first sidewall 32; however, it will be appreciated that the crossbar receiving slot 49 may be located in a variety of positions on the first sidewall 32.

Figure 3:
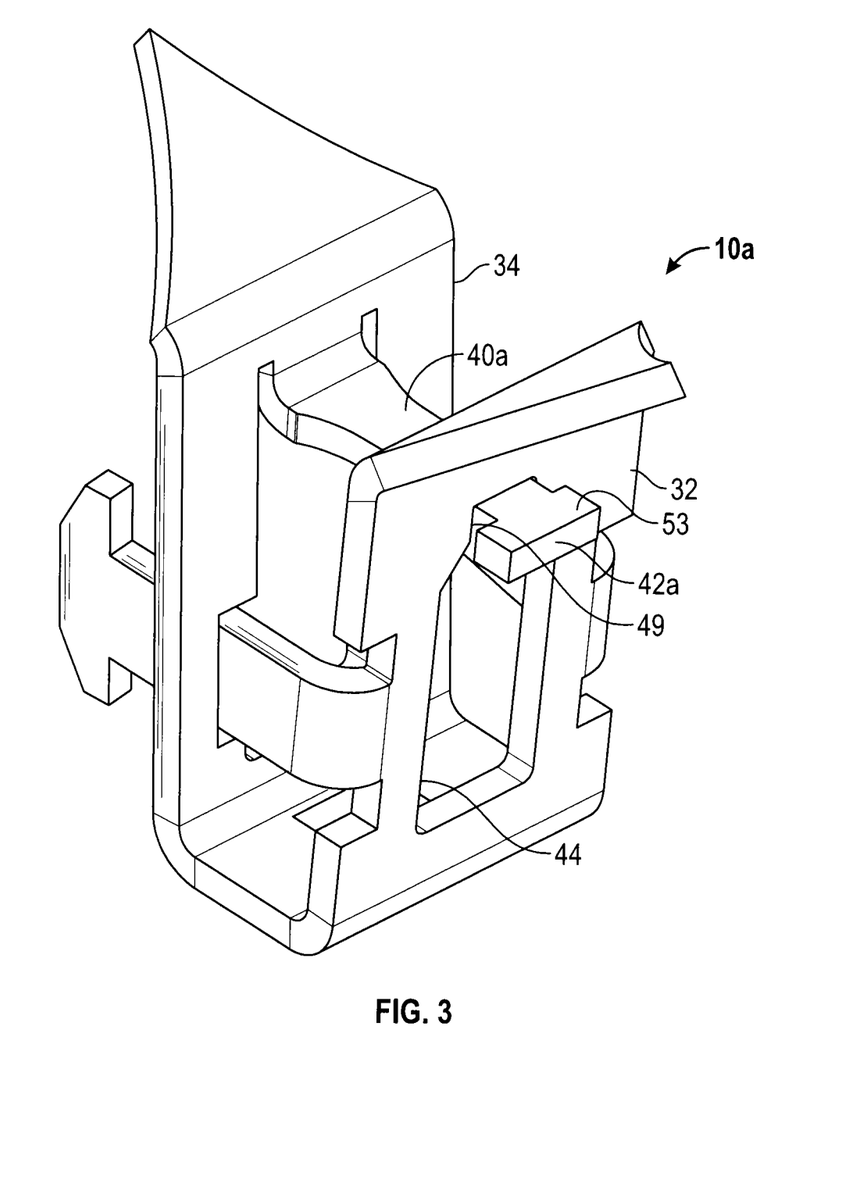
FIG. 3 is a perspective view of another embodiment of a suture anchor constructed in accordance with the inventive concepts disclosed herein.

To limit inward lateral movement of the first sidewall 32 relative to the second sidewall 34, the crossbar 40 may be provided with a support shoulder 51 (FIG. 2) formed near the free end 42 thereof. The support shoulder 51 is engageable with the first sidewall 32 when the free end 42 of the crossbar 40 is disposed in the crossbar receiving slot 49 of the crossbar window 44. FIG. 3 illustrates another embodiment of a suture anchor 10a which is similar to the suture anchor 10, except that the suture anchor 10a has a crossbar 40a provided with a support shoulder 53 formed on a free end 42a thereof. The support shoulder 53 is engageable with the first sidewall 32 when the free end 42a of the crossbar 40a is disposed in the crossbar receiving slot 49 of the crossbar window 44 so as to limit outward lateral movement of the first sidewall 32 relative to the second sidewall 34. It will be appreciated that the crossbar 40a may be formed to have the support shoulder 53 as an alternative to the support shoulder 51 illustrated in FIG. 2 or in addition to the support shoulder 51.

Returning to FIG. 1, the body 14 may be further provided with a first bone engaging portion 48 and a second bone engaging portion 50. The first bone engaging portion 48 normally extends outwardly a distance from the first sidewall 32, and the second bone engaging portion 50 normally extends outwardly a distance from the second sidewall 34. Each of the first and second bone engaging portions 48 and 50 taper to a point.

To support the first and second sidewalls 32 and 34 relative to one another, the body 14 is provided with a pair of support arms. More specifically, the body 14 has a first arm 60 and a second arm 62 extending inwardly from the first sidewall 32. The second sidewall 34 has an opening 64 formed therein which has a first side 66 and a second side 68. Notches 70a and 70b are formed along the first side 66 and the second side 68, respectively. The first and second arms 60 and 62 extend across the recess 36 and are slidably positioned in the notches 70a and 70b, respectively. Each of the first arm 60 and the second arm 62 has a head portion 72 configured to engage the second sidewall 34 to capture the first and the second arm 60 and 62 to limit outward lateral movement of the first sidewall 32 relative to the second sidewall 34. The first and second arms 60 and 62 bias outwardly to maintain the first and second arms 60 and 62 in the notches 70a and 70b.

Referring now to FIG. 2, the blank 12 for forming the body 14 is illustrated. The blank 12 may be made from any sheet material that is suitable for use as a suture anchor and is able to be bent or folded in a desired shape while maintaining a certain degree of elasticity or spring back. Examples of suitable materials include biocompatible metals and metal alloys, such as titanium, titanium alloys including Nitinol, and stainless steel, as well as plastic. The blank 12 may be made by any number of manufacturing processes including mechanical punching, laser cutting, water jet cutting, stamping, chemical etching, and photolithography, by way of example.

The blank 12 has a first end portion 80, an intermediate portion 81, a second end portion 82, a first side 84, and a second side 88. The first end portion 80 and the second end portion 82 are tapered to define the first and second bone engaging portions 48 and 50 of the body 14. The first end portion 80 of the blank 12 is further formed to have a hole 90 so as to define a protrusion 92 which when the blank 12 is folded defines the crossbar 40. The hole 90 is further formed to define the notches 94a and 94b which form the notches 70a and 70b of the body 14.

The second end portion 82 of the blank 12 is provided with a hole 96 which defines the crossbar window 44 when the blank 12 is folded to form the body 14. A pair of laterally extending arms 98a and 98b is formed to extend from the first side 84 and the second side 88, respectively. The arms 98a and 98b define the first and second arms 60 and 62.

The intermediate portion 81 of the blank 12 is provided with a central hole 99.

To form the body 14 from the blank 12, the blank 12 is folded or bent along fold line 100 to move the protrusion 92 out of a plane defined by the blank 12 and thereby form the crossbar 40. The blank 12 is further folded along fold lines 101 and 102 to move the first end portion 80 and the second end portion 82 toward one another so as to define the floor 30, the first sidewall 32, and the second sidewall 34. The blank 12 is folded along fold lines 104 and 106 so as to move the laterally extending arms 98a and 98b inwardly to one another to form the first arm 60 and the second arm 62. The blank 12 is folded along fold lines 108 and 110 to form the first and the second bone engaging portion 48 and 50.

Figure 4:
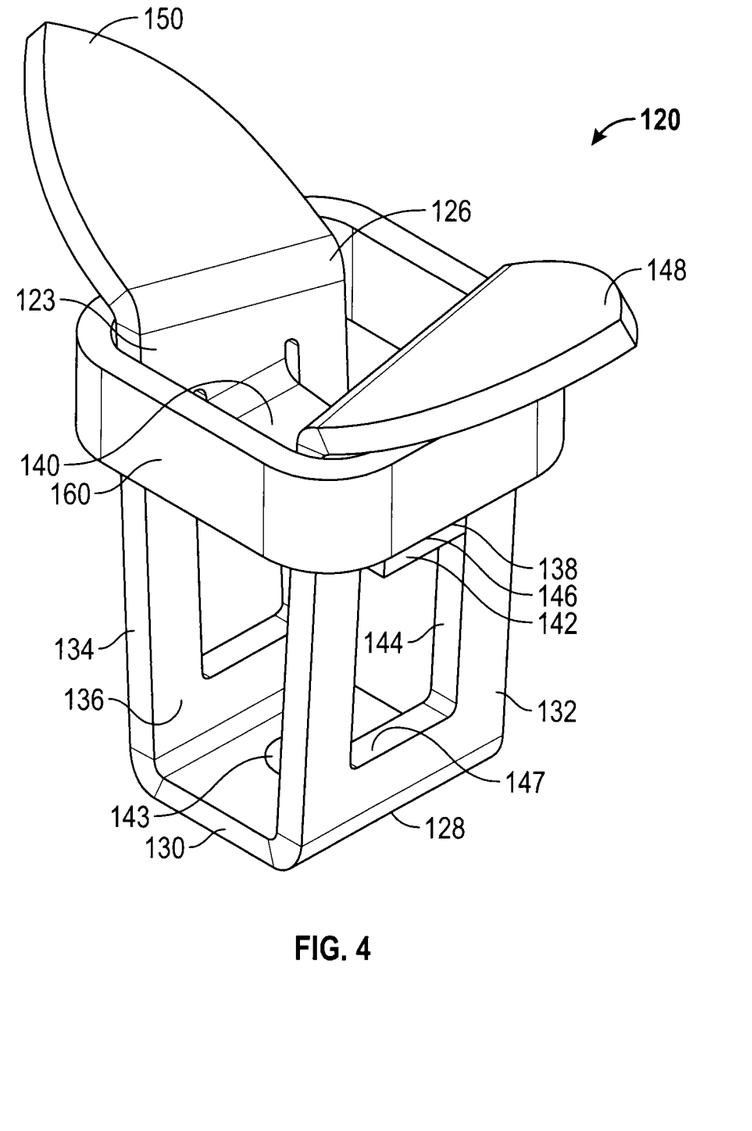
FIG. 4 is a perspective view of another embodiment of a suture anchor constructed in accordance with the inventive concepts disclosed herein.
Figure 5:
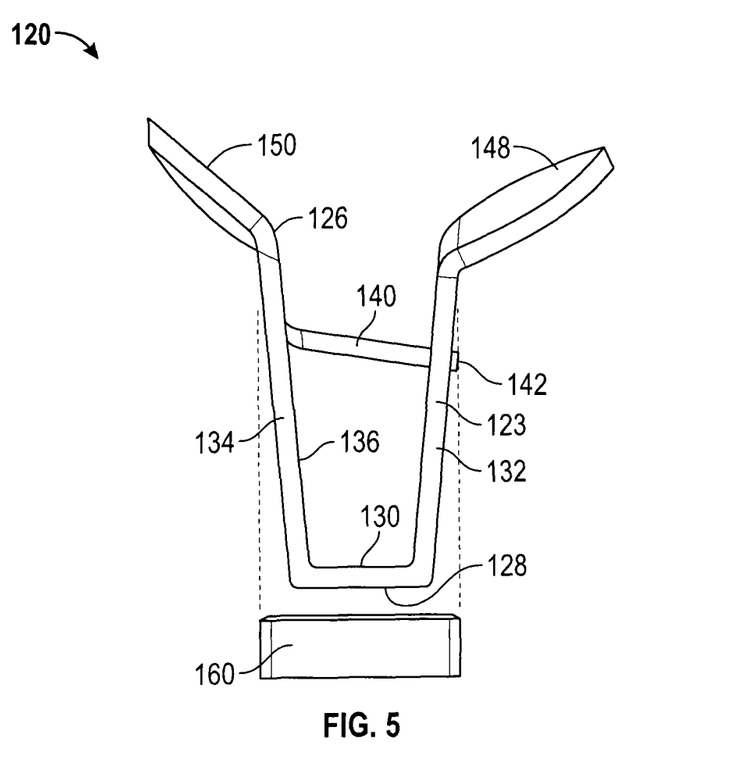
FIG. 5 is an exploded, elevational view of the suture anchor of FIG. 4.
Figure 6:
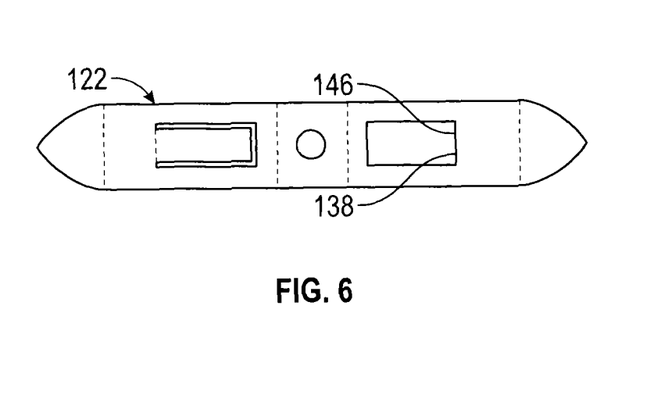
FIG. 6 is a plan view of a blank for forming a body of the suture anchor of FIGS. 4 and 5.

Referring now to FIGS. 4-6, another embodiment of a suture anchor 120 constructed in accordance with the inventive concepts disclosed herein is illustrated. The suture anchor 120 is formed from a blank 122 (FIG. 6) folded to form a body 123. The body 123 has a proximal end 126, a distal end 128, a floor 130, a first sidewall 132 extending from one end of the floor 130 toward the proximal end 126, and a second sidewall 134 extending from an opposite end of the floor 130 toward the proximal end 126. The floor 130, the first sidewall 132, and the second sidewall 134 cooperate to define a recess 136. The first sidewall 132 is provided with a transverse edge 138, and the second sidewall 134 has a crossbar 140 extending inwardly therefrom across the recess 136 such that a free end 142 of the crossbar 140 is normally disposed distally of the transverse edge 138. The floor 130 may be provided with a central opening 143 configured to receive a portion of an anchor insertion tool for deploying the suture anchor 120 in bone.

The crossbar 140 is flexible such that when a distally directed force is applied to the crossbar 140, the free end 142 of the crossbar 140 is positioned in the recess 136 and when a proximally directed force is applied to the crossbar 140, the free end 142 of the crossbar 140 engages with the transverse edge 138 to limit proximal motion of the crossbar 140.

The first sidewall 132 is provided with a crossbar window 144 in communication with the recess 136. The crossbar window 144 has a proximal side 146 and a distal side 147 where the proximal side 146 of the crossbar window 144 defines the transverse edge 138. The crossbar 140 extends across the recess 136 such that the free end 142 of the crossbar 140 is normally disposed in the crossbar window 144.

The body 123 is further provided with a first bone engaging portion 148 and a second bone engaging portion 150. The first bone engaging portion 148 normally extends outwardly a distance from the first sidewall 132, and the second bone engaging portion 150 normally extends outwardly a distance from the second sidewall 134. Each of the first and second bone engaging portions 148 and 150 taper to a point. As illustrated in FIG. 4, the first bone engaging portion 148 and the second bone engaging portion 150 may be angled or inclined similar to that of a fan blade, to enable the suture anchor 120 to be installed or removed from bone with torsional force.

To support the first and second sidewalls 132 and 134 relative to one another, the suture anchor 120 further includes a collar 160 extending about the first sidewall 132 and the second sidewall 134 to limit outward lateral movement of the first sidewall 132 relative to the second sidewall 134. In one embodiment, the collar 160 may be fixed to one or both of the first and second sidewalls 132 and 134. In another embodiment, the collar 160 may be pressed on the first and second sidewall 132 and 134.

Figure 7:
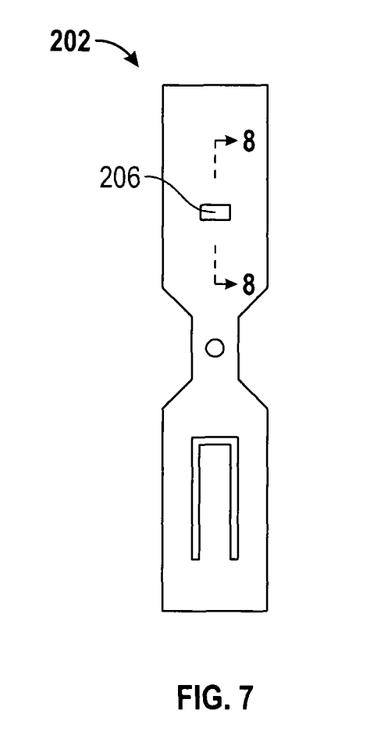
FIG. 7 is a plan view of another embodiment of a blank.
Figure 8:
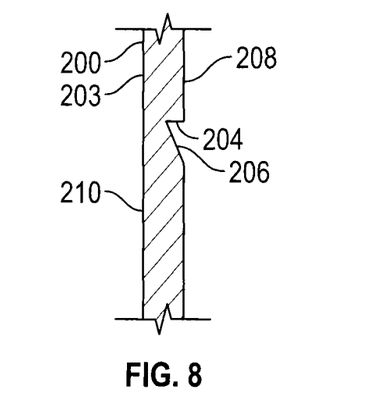
FIG. 8 is a cross-sectional view taken along line 8-8 of FIG. 7.

FIGS. 7 and 8 illustrate another embodiment of a suture anchor 200 constructed in accordance with the inventive concepts disclosed herein. The suture anchor 200 is formed from a blank 202 (FIG. 7) folded to form a body 203. The body 203 is similar in form and construction to the body 123 described above except the body 203 has a transverse edge 204 defined by a proximal surface of a notch 206 formed in an interior surface 208 of a first sidewall 210.

Figure 9:
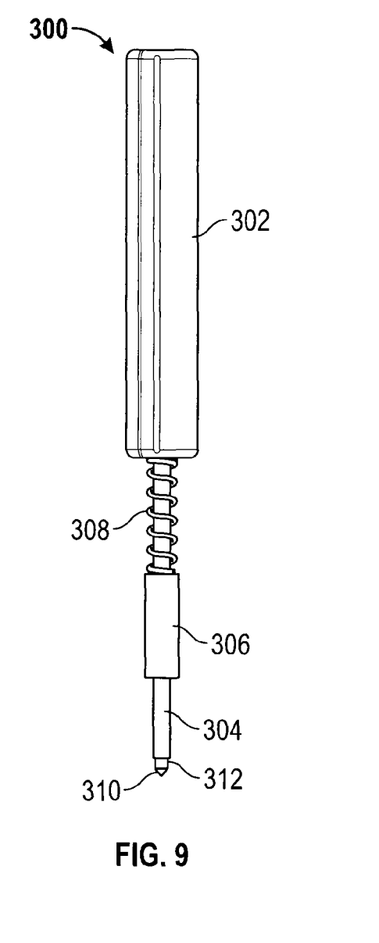
FIG. 9 is an elevational view of an anchor insertion tool shown in a retracted position.
Figure 10:
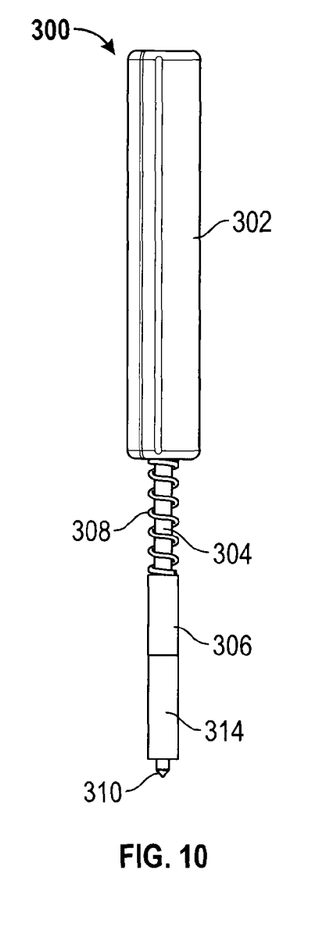
FIG. 10 is an elevational view of the anchor insertion tool of FIG. 9 with an anchor cartridge shown attached thereto.
Figure 11:
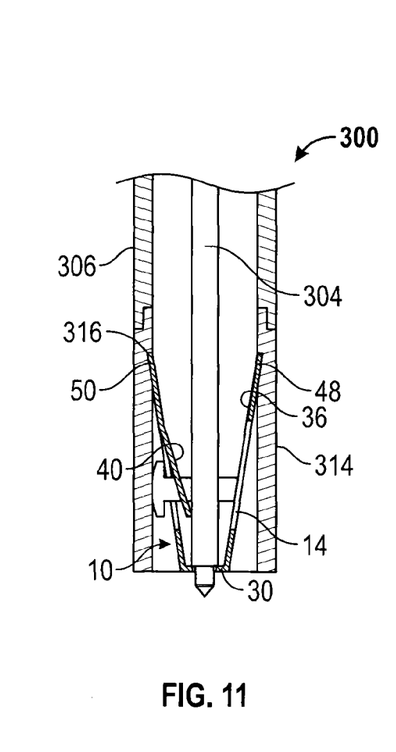
FIG. 11 is a sectional view of the cartridge attached to the anchor insertion tool of FIG. 10 illustrating the suture anchor of FIG. 1 housed therein.

Referring now to FIGS. 9-11, an example of an anchor insertion tool 300 that may be used to insert the suture anchors 10, 120, and 200 into bone is illustrated. With reference to use with the suture anchor 10, the anchor insertion tool 300 has a handle 302, a drive shaft 304, a spacer sleeve 306, and a spring 308. The drive shaft 304 extends from the handle 302 and is dimensioned to be disposed in the recess 36 of the body 14. The drive shaft 304 has a tapered tip 310 that is sized to be received through the central opening 43 of the floor 30 of the body 14 so that a shoulder 312 defined on the drive shaft 304 engages the floor 30. The drive shaft 304 is slidably disposed through the spacer sleeve 306. The spring 308 is positioned between the handle 302 and the spacer sleeve 306 to bias the drive shaft 304 in a retracted position relative to the spacer sleeve 306, as illustrated in FIGS. 9 and 10.

A distal end of the spacer sleeve 306 is adapted to be detachably connected to a cartridge 314 through a mechanical connection such as a threaded connection. The cartridge 314 may be a sleeve member similar in configuration to the spacer sleeve 306 for housing the suture anchor 10 prior to deployment into bone. As illustrated in FIG. 11, the suture anchor 10 is housed in the cartridge 314 with the bone engaging portions 48 and 50 folded upwardly to facilitate insertion of the suture anchor 10 into the bone. The cartridge 314 may be provided with a shoulder or stop 316 for engaging the ends of the first and second bone engaging portion 48 and 50. When the suture anchor 10 is loaded into the cartridge 314, the first bone engaging portion 48 and the second bone engaging portion 50 engage the stop 316. When the cartridge 314, with the loaded suture anchor 10, is connected to the spacer sleeve 306, the drive shaft 304 is disposed through the recess 36 of the body 14 so as to cause the crossbar 40 to be deflected downwardly so as to allow the drive shaft 304 to be inserted through the recess 36 and engage the floor 30.

Figure 12:
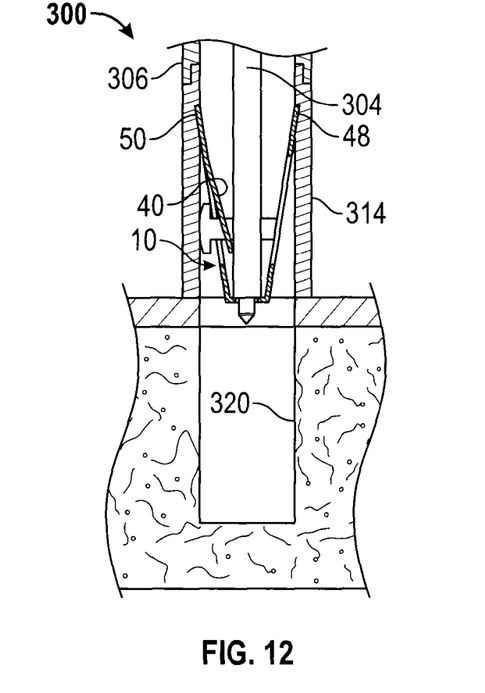
FIGS. 12-14 are diagrammatical sectional views of the suture anchor of FIG. 1 being installed in a bone with the anchor insertion tool of FIG. 10.
Figure 13:
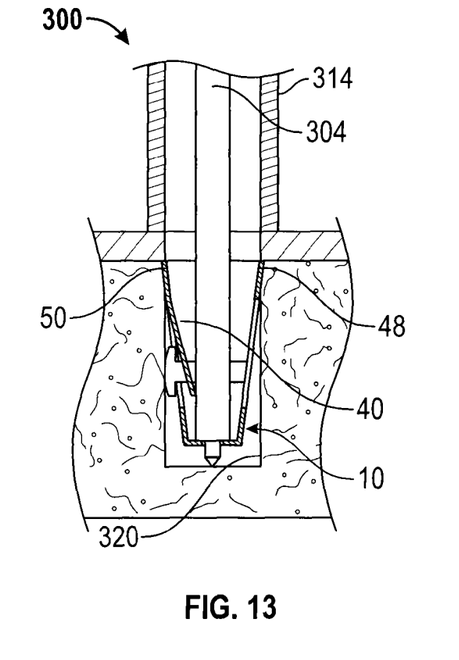
Figure 14:
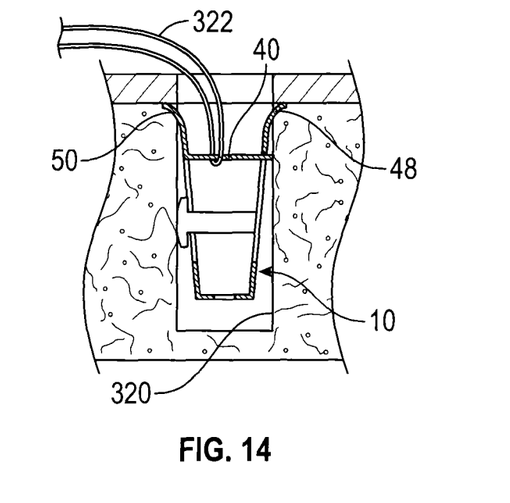

Referring now to FIGS. 12-14, the suture anchor 10 is inserted into bone as follows. First, a hole 320 for receiving the suture anchor 10 is formed in the bone using any suitable instrument, such as a drill or a punch. The cartridge 314 with the suture anchor 10 loaded therein is attached to the spacer sleeve 306 of the anchor insertion tool 300. The anchor insertion tool 300 is positioned over the hole 320 so that the distal end of the cartridge 314 contacts the bone surface. A distally directed force is then applied to the handle 302 of the anchor insertion tool 300 causing the drive shaft 304 to travel in a distal direction through the spacer sleeve 306 and the cartridge 314 compressing spring 308 and driving the suture anchor 10 into the hole 320. The anchor insertion tool 300 is then removed from the hole 320. The removal of the distally directed force from the anchor insertion tool 300 and the lateral containment of the cartridge 314 allows the first bone engaging portion 48 and the second bone engaging portion 50 to expand outwardly so that when an upward force is applied to the suture anchor 10, the first bone engaging member 48 and the second bone engaging portion 50 become embedded under the cortical bone layer, securing the suture anchor 10 within the hole.

If desired, one or more sutures may be attached to the suture anchor prior to deployment in the bone. Otherwise, the configuration of the suture anchor 10 enables one or more sutures 322 (FIG. 14) to be attached to the suture anchor 10 after the suture anchor 10 has been deployed in the bone. The sutures 322 may be attached to the suture anchor 10 in any suitable fashion. By way of example, the sutures may positioned about the crossbar 40 with a suture threader such as disclosed in U.S. Publication. No. 2009/0088798, which is hereby expressly incorporated herein by reference.

From the above description, it is clear that the inventive concepts disclosed and claimed herein are well adapted to carry out the objects and to attain the advantages mentioned herein, as well as those inherent in the invention. While exemplary embodiments of the inventive concepts have been described for purposes of this disclosure, it will be understood that numerous changes may be made which will readily suggest themselves to those skilled in the art and which are accomplished within the spirit of the inventive concepts disclosed and/or as defined in the appended claims.

What is claimed is:

1. A method of forming a suture anchor, comprising:
folding a one piece blank formed from a planar sheet of material to form a body having a proximal end, a distal end, a floor positioned at the distal end, a first sidewall extending from one end of the floor toward the proximal end, a second sidewall extending from an opposite end of the floor toward the proximal end, a recess defined by the floor, the first sidewall, and the second sidewall, and a transverse edge formed on the first sidewall; and
folding the one piece blank to form a crossbar extending inwardly from the second sidewall across the recess such that a free end of the crossbar is normally disposed distally of the transverse edge of the body,
wherein the crossbar is flexible such that when a distally directed force is applied to the crossbar, the free end of the crossbar is positionable in the recess and when a proximally directed force is applied to the crossbar, the free end of the crossbar is engageable with the transverse edge to limit proximal motion of the crossbar.

2. The method of claim 1, wherein the one piece blank has an opening and wherein the one piece blank is folded so that the opening defines a crossbar window through the first sidewall in communication with the recess, the crossbar window having a proximal side and a distal side, the proximal side of the crossbar window defining the transverse edge of the of the body.

3. The method of claim 2, wherein the crossbar has a support shoulder near the free end thereof, the support shoulder being engageable with the first sidewall when the free end of the crossbar is disposed in the crossbar window to limit inward lateral movement of the first sidewall relative to the second sidewall.

4. The method of claim 2, wherein the one piece blank is folded so that the free end of the crossbar is normally disposed in the crossbar window.

5. The method of claim 1, wherein the one piece blank has a central hole, and wherein the one piece blank is folded so that the central hole defines a central opening through the floor configured to receive a driver for deploying the anchor in bone.

6. The method of claim 1, wherein the one piece blank is folded so that the second sidewall has an opening formed therein, the opening having a first side and a second side and having a notch formed along the first side, wherein the body further has an arm extending inwardly from the first sidewall, across the recess, and positioned in the notch, the arm having a head portion configured to engage the second sidewall to limit outward lateral movement of the first sidewall relative to the second sidewall.

7. The method of claim 6, wherein the one piece blank is folded so that the arm is outwardly biased.

8. The method of claim 1, further comprising the step of disposing a collar about the first sidewall and the second sidewall to limit outward lateral movement of the first sidewall relative to the second sidewall.

\* \* \* \* \*